United States Patent

Bianchetti et al.

[11] Patent Number: 5,879,584
[45] Date of Patent: Mar. 9, 1999

[54] PROCESS FOR MANUFACTURING AQUEOUS COMPOSITIONS COMPRISING PERACIDS

[75] Inventors: Giulia Ottavia Bianchetti; Stefano Scialla, both of Rome; Sandro Campestrini, Trento; Fulvio Di Furia, Padua, all of Italy

[73] Assignee: The Procter & Gamble Company, Cincinnati, Ohio

[21] Appl. No.: 809,303

[22] PCT Filed: Sep. 8, 1995

[86] PCT No.: PCT/US95/11284

§ 371 Date: Jun. 13, 1997

§ 102(e) Date: Jun. 13, 1997

[87] PCT Pub. No.: WO96/07640

PCT Pub. Date: Mar. 14, 1996

[30] Foreign Application Priority Data

Sep. 10, 1994 [EP] European Pat. Off. .............. 94202608

[51] Int. Cl.⁶ .............................. C01B 15/10; C11D 3/395
[52] U.S. Cl. ................. 252/186.23; 252/186.38; 562/4; 562/2; 562/3; 510/312
[58] Field of Search ................. 562/2, 3, 4; 252/186.22, 252/186.23, 186.38, 186.39; 510/312

[56] References Cited

U.S. PATENT DOCUMENTS

| | | | |
|---|---|---|---|
| 4,129,517 | 12/1978 | Eggensperger et al. ............. | 8/111 |
| 4,292,192 | 9/1981 | Hooper et al. ............. | 252/132 |
| 4,297,298 | 10/1981 | Crommelynck et al. ............. | 568/559 |
| 4,391,876 | 7/1983 | Tamosausksa et al. ............. | 428/392 |
| 4,435,473 | 3/1984 | Tamosauskas et al. ............. | 428/378 |
| 4,440,885 | 4/1984 | Tamosauskas et al. ............. | 524/57 |
| 4,613,452 | 9/1986 | Sanderson ............. | 252/186.23 |
| 4,659,519 | 4/1987 | Ku ............. | 562/4 |
| 4,666,622 | 5/1987 | Martin et al. ............. | 252/99 |
| 4,680,145 | 7/1987 | Taylor et al. ............. | 562/4 |
| 4,917,815 | 4/1990 | Beifuss et al. ............. | 252/186.23 |
| 5,409,632 | 4/1995 | Showell et al. ............. | 510/372 |
| 5,616,281 | 4/1997 | Hardy et al. ............. | 252/186.38 |
| 5,681,805 | 10/1997 | Scheuing et al. ............. | 510/277 |
| 5,713,962 | 2/1998 | Scialla et al. ............. | 8/111 |

FOREIGN PATENT DOCUMENTS 0 598 170 A1  11/1992  European Pat. Off. .......... C11D 3/39

OTHER PUBLICATIONS

U.S application No. 08/722,038, Pilotti et al., filed as a PCT US 95/04020 on Mar. 30, 1995.

U.S. application No. 08/826,321, Scialla et al, PCT US 93/10431 on Oct. 29, 1993.

Primary Examiner—Joseph D. Anthony
Attorney, Agent, or Firm—Robert B. Aylor

[57] ABSTRACT

A process for manufacturing an aqueous composition of a peracid by reacting an acid anhydride with concentrated hydrogen peroxide. Preferably the aqueous peracid composition is further converted into an emulsion having improved stability wherein said emulsion contains a surfactant having an HLB above 11 and a surfactant having an HLB below 11.

4 Claims, No Drawings

PROCESS FOR MANUFACTURING AQUEOUS COMPOSITIONS COMPRISING PERACIDS

This is a 35 U.S.C. §371 Application from PCT/US95/11284, filed Sep. 8, 1995.

TECHNICAL FIELD

The present invention relates to a process for manufacturing aqueous compositions comprising peracids (percarboxylic acids) and more particularly to a process for manufacturing aqueous emulsions comprising a peracid, or mixtures thereof. The aqueous compositions prepared according to the process of the present invention are particularly suitable to be used in various applications such as in laundry applications, or as hard-surface cleaners or as carpet cleaners, or as denture cleaners or as disinfecting compositions in general.

BACKGROUND

A great variety of cleaning compositions have been described in the art. Indeed, compositions comprising hydrogen peroxide, and/or water soluble sources thereof including peracids are widely used. In order to provide such compositions comprising peracids, it is common practice to use peracid precursors as a source of said peracids. Indeed, peracids are not commonly commercially available, and if available may not be used satisfactorily, as said peracids are not stable and tend to decompose dramatically during storage, this even before their incorporation into a composition. Compositions containing such peracids can be made by a variety of methods employing reactions between hydrogen peroxide and the corresponding peracid precursors, i.e. the corresponding acids. However, such methods are not fully satisfying. Indeed, there is a need for the development of processes for manufacturing aqueous compositions with better productivity in several respects, e.g. formulators are looking for a process which allows to incorporate higher amounts of peracids in a finished product, starting from a given amount of the corresponding precursors.

It is therefore an object of the present invention to provide a process for improving the efficiency of producing peracids.

We have now found that this object can be efficiently met by reacting a concentrated hydrogen peroxide solution with, as the precursor of the peracid, the corresponding anhydride instead of the corresponding acid. Indeed, it has been found that a faster preparation as well as a higher yield of said peracid are achieved when reacting with a concentrated hydrogen peroxide solution, the corresponding anhydride, as compared to reacting with said concentrated hydrogen peroxide solution, the corresponding acid instead of said corresponding anhydride, as said precursor of said peracid. In other words, it has been found that a process which comprises the step of reacting the corresponding precursor being in an anhydride form with a concentrated hydrogen peroxide solution leads to faster preparation of compositions comprising a higher amount of said peracid, starting from a given amount of said precursor.

An advantage of a process according to the present invention is that it allows for great flexibility in formulating and provides compositions comprising peracid suitable to be used in the most efficient manner by the consumer. Indeed, such a composition can be a raw material composition, or can be a fully formulated detergent composition comprising additional ingredients such as those commonly used in the detergent field. Preferred herein is a process which allows to provide compositions with high amounts of peracids, said compositions being in the form of emulsions. Indeed, an advantage associated with the emulsions obtained according to a process of the present invention is that such compositions not only incorporate a higher amount of a peracid, starting from a given amount of the corresponding anhydride but also allow to provide a finished product having improved stability during storage, i.e. in emulsions the rate of decomposition of peracids contained therein is reduced, as compared to compositions being not in the form of emulsions.

Processes for the preparation of compositions or even emulsions comprising a bleach have been disclosed in the art. For instance, EP-A-598170 discloses the use of emulsions to formulate compositions comprising $H_2O_2$ and a hydrophobic bleach activator (ATC), wherein the bleach activator is kept separate from $H_2O_2$. This patent application also discloses the possible use of a water-soluble source of $H_2O_2$ including peracids but no indication is given about how to provide them. Indeed, although a general process for the preparation of emulsions is disclosed, none of the process steps disclosed therein indicates how to incorporate peracids, or to use peracid precursors in their anhydride form.

WO 93/0516 to Interox discloses a process for the preparation of a dilute aqueous solution comprising an hydroxyaliphatic peroxycarboxylic acid having no more than 7 carbon atoms in which in a first step a concentrated aqueous solution of said peroxycarboxylic acid precursor, i.e. an hydroxyaliphatic carboxylic acid, is mixed with a concentrated hydrogen peroxide solution in presence if necessary of a strong acid as a catalyst, in a second step the mixture is stored until the concentration of said peroxycarboxylic acid has approached its maximum; then the mixture is diluted in water. WO 93/0516 does not disclose the use of any peroxyacid precursor being in its anhydride form.

EP 188 025 mentions that the peroxymonosulphuric acid used in the compositions disclosed therein are commercially available in an aqueous solution as Caro's acid prepared by addition of concentrated hydrogen peroxide to concentrated sulphuric acid. Thus, the peracid precursors disclosed are the corresponding acids whereas in the present invention the corresponding anhydrides are used.

SUMMARY OF THE INVENTION

The present invention is a process for manufacturing an aqueous composition comprising a peracid, or mixtures thereof, said process comprising the step of forming said peracid by reacting the corresponding anhydride with a solution of hydrogen peroxide comprising at least 3 moles hydrogen peroxide per molar equivalent of said corresponding anhydride.

The present invention also encompasses a process for manufacturing an aqueous composition comprising a peracid, or mixtures thereof, wherein said peracid is emulsified in a surfactant system comprising at least a hydrophilic surfactant having an HLB above 11 and at least a hydrophobic surfactant having an HLB below 11, said process comprising the steps of:

1—preparing an aqueous composition of said peracid by reacting the corresponding anhydride with a solution of hydrogen peroxide comprising at least 3 moles hydrogen peroxide per molar equivalent of said corresponding anhydride;

2—preparing a hydrophobic mixture which comprises at least said hydrophobic surfactant;

3—preparing a hydrophilic mixture which comprises at least water and said hydrophilic surfactant;

4—mixing said peracid-comprising composition obtained in step 1 in said hydrophobic mixture if said peracid is a hydrophobic peracid or in said hydrophilic mixture if said peracid is a hydrophilic peracid;

5—then mixing together said hydrophobic mixture and said hydrophilic mixture, and wherein steps 2 and 3 may be performed in any order.

DETAILED DESCRIPTION OF THE INVENTION

The process according to the present invention is a process for manufacturing an aqueous composition comprising a peracid, said process comprising the step of forming said peracid by reacting the corresponding anhydride with a concentrated hydrogen peroxide solution.

As a first essential element, the process of the present invention requires the use of "the corresponding anhydride". By "the corresponding anhydride" it is to be understood herein that in order to obtain a composition comprising a desired peracid, the peracid precursor to be used herein is the anhydride corresponding to this peracid. Said anhydride by reaction with a concentrated hydrogen peroxide solution allows to obtain said peracid-comprising composition.

In the present invention the anhydride which is peroxidized to obtain the corresponding peracid may be any anhydride having the following formula, or mixtures thereof:

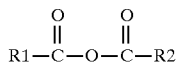

wherein $R_1$ and $R_2$ are linear or branched alkyl or aryl groups having of from 1 to 20 carbon atoms. Said anhydrides include symmetric anhydrides, i.e. anhydrides of the above formula wherein $R_1$ and $R_2$ are identical, as well as asymmetric anhydrides, i.e. anhydrides of the above formula wherein $R_1$ is different from $R_2$. Depending on the length of the carbon chain said symmetric and/or asymmetric anhydrides may be classified as hydrophilic anhydrides or as hydrophobic anhydrides. Accordingly, the symmetric or asymmetric anhydrides as defined herein above wherein $R_1$ and $R_2$ are linear or branched alkyl or aryl groups having of from 1 to 4 carbon atoms, are hydrophilic anhydrides. Preferred hydrophilic anhydrides to be used according to the present invention have for $R_1+R_2$ a maximum of 8 carbon atoms. In other words, both such an anhydride and its corresponding peracid are soluble in the hydrophilic phase of an emulsion as defined herein after. Also, the symmetric or asymmetric anhydrides as defined herein above wherein $R_1$ and/or $R_2$ are linear or branched alkyl or aryl groups having of from 5 to 20 carbon atoms, are hydrophobic anhydrides. In other words, both such an anhydride and its corresponding peracid are soluble in the hydrophobic phase of an emulsion as defined hereinafter.

Accordingly examples of hydrophilic anhydrides are acetic anhydride (commercially available as a liquid from Aldrich), succinic anhydride (commercially available in solid form from Aldrich), and examples of hydrophobic anhydrides are pimelic anhydride (commercially available in solid form from Chemie Uetikon), adipic anhydride, azelaic anhydride, stearic anhydride (commercially available as solids for example from Novachem) and myristic anhydride.

Other hydrophilic anhydrides particularly suitable to be used as the corresponding anhydride of the present invention include cyclic anhydrides having the following formula, or mixtures thereof:

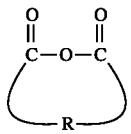

wherein R is an alkyl carbon chain having from 1 to 4 carbon atoms, said cyclic anhydrides include the ones with or without substituents on their ring. An example of such a hydrophilic anhydride is glutaric (cyclic) anhydride commercially available in solid form from Aldrich.

Other hydrophobic anhydrides particularly suitable to be used as the corresponding anhydride include polymeric anhydrides having the following formula, or mixtures thereof:

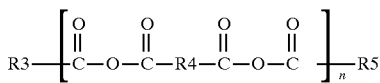

wherein R3, R4, R5 are linear or branched alkyl chains having from 1 to 20 carbon atoms, or aryl groups having from 1 to 20 carbon atoms and wherein n is in the range from 1 to 20.

As a second essential element, the process of the present invention requires the use of a concentrated hydrogen peroxide solution, i.e. a solution of hydrogen peroxide comprising at least 3 moles hydrogen peroxide per molar equivalent of the corresponding anhydride, preferably at least 10 and more preferably at least 15.

Accordingly in the preferred embodiment, the corresponding anhydride is mixed with a solution of hydrogen peroxide comprising from 20% to 90% by weight of said hydrogen peroxide, more preferably from 25% to 80% and most preferably from 30% to 70%.

The temperature at which the present peroxidation reaction is conducted depends on the concentration of hydrogen peroxide used. If hydrogen peroxide is very concentrated (e.g., 70%), the reaction is preferably conducted around 0° C. If it is less concentrated (e.g., 36%), the reaction is preferably conducted at room temperature or higher. For convenience, coupled with safety considerations, the reaction temperature is maintained in many embodiments in the range that is from 0° C. to 40° C. Also, the present peroxidation reaction is conducted in the acidic range at a pH range from 0 to 4, preferably of from 0 to 2.

The process of the present invention allows to obtain aqueous compositions comprising a peracid, or mixtures thereof. Said peracid-comprising compositions comprise from 0.01% to 50% by weight of the total composition of said peracid, or mixtures thereof, preferably from 0.01% to 40%, and more preferably from 0.1% to 30%. Said compositions further comprise hydrogen peroxide which has not reacted with the anhydride. Generally, said compositions comprise from 1% to 90% and more preferably from 1% to 70% of the total composition of said hydrogen peroxide. Said compositions may be used as a raw material composition in applications such as hard-surface cleaning, toilet bowl cleaning, carpet cleaning, laundry applications as well as denture cleaning.

The process of the present invention comprising the step of forming said peracid-comprising composition, as herein above mentioned, may further comprise a dilution step where said composition is diluted with water or an aqueous composition. The extent of dilution is at the discretion of the process operator. It is often convenient to dilute until the composition has a peracid concentration of from 0.01% to 30% by weight of the total composition, preferably of from 0.1% to 20%. Accordingly said compositions herein also comprise from 0.5% to 20% by weight of said hydrogen peroxide, more preferably from 2% to 15% and most preferably from 3% to 10%. The process of the present invention allows accordingly to manufacture not only raw material compositions but also fully formulated detergent compositions, i.e. compositions incorporating further ingredients commonly used in the detergent field. Indeed, in order to provide such a detergent composition said aqueous composition used in the process of the present invention apart from water further comprises optional ingredients such as perfumes, dyes, builders, chelants, pigments, enzymes, dye transfer inhibitors, solvents, buffering agents and the like, or mixtures thereof.

The dilution stage is conducted at or around ambient temperature. The dilution water solution often has a temperature of from 5° C. to 25° C. It is desirable to effect the dilution soon after the point at or near which the maximum peracid concentration has been obtained. The compositions obtained according to the process of the present invention can be monitored as described herein after. Indeed, it is possible according to the process of the present invention to attain a peracid concentration that is at or near a maximum in a period of less than 5 hours and advantageously a period of not greater than 5 minutes is often sufficient in particular in very acidic environments (e.g., pH=0–1), starting from the moment where anhydride is mixed with a concentrated hydrogen peroxide solution.

An advantage associated with the process of the present invention is that a faster preparation with a higher yield of peracids is obtained starting from a given amount of the corresponding anhydride without the need of any catalyst (such as strong acids) as compared to peracids preparation from the correspondent acid. Thus the process of the present invention preferably does not use a catalyst to help the conversion of peracid precursors to the corresponding peracids. Also a further advantage associated with the process of the present invention is that a faster preparation with a higher yield of peracids is obtained without the use of elevated reaction temperatures.

By "faster preparation" it is meant herein that, starting from a given amount of a peracid precursor, the time needed to reach the maximum peracid concentration (time needed to obtain entirely peroxidation of the carboxylic anhydride group or groups) is shorter when reacting the corresponding anhydride, as said peracid precursor, with a concentrated hydrogen peroxide solution as compared to reacting the corresponding acid with said concentrated hydrogen peroxide solution. This can be evaluated by monitoring the peracid content of a reaction mixture. For example samples of a reaction mixture can be periodically analyzed for the peracid available oxygen (often abbreviated to Avox). Test method to evaluate peracid Avox is done via chromatography (see F. Di Furia et. alt., Gas-liquid chromatography method for determination of peracids, Analyst, vol. 109, August 1984, p. 985–987; or ibidem vol. 113, May 1988, p. 793–795).

By "yield" it is to be understood herein the percentage of peracid obtained calculated with respect to the corresponding peracid precursor, i.e. corresponding anhydride. The following equation is applied to calculate said yield:

(peracid concentration/corresponding precursor peracid concentration)*100=% yield In said equation the concentration are expressed in mole/liter. Indeed, it has surprisingly been found that a higher yield of peracid is provided with the present process starting from a given amount of the corresponding anhydride and reacting it with a concentrated hydrogen peroxide solution, as compared to a similar process wherein the corresponding precursor is the corresponding acid instead of the corresponding anhydride.

It is preferred herein to manufacture detergent compositions in the form of emulsions. Accordingly, the process for manufacturing aqueous compositions comprising a peracid further comprises additional steps so as to provide aqueous compositions being in the form of emulsions. In said aqueous compositions said peracids is emulsified by means of a surfactant system of at least two different surfactants, i.e. at least a hydrophobic surfactant having an HLB below 11 and at least one hydrophilic surfactant having an HLB above 11. Indeed, said two different surfactants in order to form emulsions which are stable must have different HLB values (hydrophilic lipophilic balance), and preferably the difference in value of the HLBs of said two surfactants is at least 1, preferably at least 3.

An advantage associated with an emulsion obtained according to the process of the present invention is that said composition comprises a higher amount of peracid, starting from a given amount of the corresponding anhydride and that the decomposition rate of said peracid is reduced during storage, i.e. improved stability is achieved. By "improved stability" it is to be understood herein that the time required to obtain half of the initial concentration of peracids in a given composition being in the form of an emulsion is greater than the time required to obtain half of the initial concentration of peracids in the same composition but which is not in the form of an emulsion. Peracid concentration such as for instance glutaric peracid can be measured as per the article mentioned herein above.

Thus the present invention also encompasses a process for manufacturing an aqueous composition comprising a peracid, or mixtures thereof, wherein said peracid is emulsified by a surfactant system comprising at least a hydrophilic surfactant having an HLB above 11 and at least a hydrophobic surfactant having an HLB below 11, said process comprising the following steps:

In a first step a peracid-comprising composition is prepared according to the present invention, as herein before described, i.e. by mixing the corresponding anhydride with a concentrated hydrogen peroxide solution.

In a second step, a hydrophobic mixture is prepared which comprises at least said hydrophobic surfactant. Said hydrophobic mixture preferably further comprises other hydrophobic ingredients which are to be formulated in the composition such as perfumes, solvents, enzymes, bleach activators, polymers and said peracid-comprising composition if said peracid is hydrophobic.

In a third step, a hydrophilic mixture is prepared which comprises at least water and said hydrophilic surfactant. Said hydrophilic mixture preferably further comprises other hydrophilic ingredients which are to be formulated in the composition such as dyes, hydrophilic optical brighteners, builders, chelants, buffering agents and said peracid-comprising composition if said peracid is hydrophilic.

Indeed, in the process of the present invention the peracid-comprising composition obtained in the first step is mixed in the hydrophobic mixture if said peracid is hydrophobic or in the hydrophilic mixture is said peracid is hydrophilic.

Naturally, said second and said third steps can be performed in any order, i.e. third step second is also suitable.

Finally in another step of the process according to the present invention, said hydrophobic mixture and said hydrophilic mixture are mixed together.

In fact the present invention also encompasses a process wherein various peracid-comprising compositions may be prepared, i.e. at least a peracid-comprising composition wherein said peracid is hydrophilic and at least a peracid-comprising composition wherein said peracid is hydrophobic, and wherein said peracid-comprising compositions are introduced in either the hydrophobic or the hydrophilic mixture depending on their respective feature, i.e. hydrophilic or hydrophobic.

According to the process of the present invention used for manufacturing emulsions apart from the concentrated hydrogen peroxide solution used in the reaction step to form the peracid-comprising composition there is no need to further introduce hydrogen peroxide in said emulsions. Accordingly said emulsions comprise from 0.5% to 20% by weight of said total emulsion of hydrogen peroxide, preferably from 2% to 15%, most preferably from 3% to 10%. Preferred emulsions obtained according to the process of the present invention comprise from 0.01% to 30% by weight of said total composition of a peracid, or mixtures thereof, preferably from 0.1% to 20%, and more preferably from 0.1% to 10%.

The compositions obtained according to the process of the present invention comprise from 1% to 50% by weight of the total composition of said hydrophilic and hydrophobic surfactants, preferably from 2% to 40% and more preferably from 3% to 30%. Said compositions comprise at least from 0.1% by weight of the total composition of said hydrophobic surfactant, preferably at least 1% and more preferably at least 2% and at least from 0.1% by weight of the total composition of said hydrophilic surfactant, preferably at least 1% and more preferably at least 2%.

Preferred to be used in the process of the present invention to obtain aqueous compositions are the hydrophobic nonionic surfactants and hydrophilic nonionic surfactants. Said hydrophobic nonionic surfactants to be used herein have an HLB below 11, preferably below 10, more preferably below 8 and said hydrophilic surfactants have an HLB above 11, preferably above 12, more preferably above 13.

Suitable nonionic surfactants for use herein include alkoxylated fatty alcohols preferably, fatty alcohol ethoxylates and/or propoxylates. Indeed, a great variety of such alkoxylated fatty alcohols are commercially available which have very different HLB values (hydrophilic lipophilic balance). The HLB values of such alkoxylated nonionic surfactants depend essentially on the chain length of the fatty alcohol, the nature of the alkoxylation and the degree of alkoxylation. Hydrophilic nonionic surfactants tend to have a high degree of alkoxylation and a short chain fatty alcohol, while hydrophobic surfactants tend to have a low degree of alkoxylation and a long chain fatty alcohol. Surfactants catalogs are available which list a number of surfactants including nonionics, together with their respective HLB values.

Suitable chemical processes for preparing the nonionic surfactants for use herein include condensation of corresponding alcohols with alkylene oxide, in the desired proportions. Such processes are well known to the man skilled in the art and have been extensively described in the art. As an alternative, a great variety of alkoxylated alcohols suitable for use herein is commercially available from various suppliers.

Apart from hydrophobic and hydrophilic surfactants being nonionic surfactants any other types of surfactants known in the art and able to form emulsions may be used according to the present invention.

Other suitable hydrophilic surfactants to be used in the present invention may be anionic surfactants in particular sulfonate and sulfate surfactants. The like anionic surfactants are well-known in the art and have found wide application in commercial detergents. These anionic surfactants include the C8–C22 alkyl benzene sulfonates (LAS), the C8–C22 alkyl sulfates (AS), unsaturated sulfates such as oleyl sulfate, the C10–C18 alkyl alkoxy sulfates (AES) and the C10–C18 alkyl alkoxy carboxylates. The neutralizing cation for the anionic synthetic sulfonates and/or sulfates is represented by conventional cations which are widely used in detergent technology such as sodium, potassium or alkanolammonium.

The compositions obtained according to the process of the present invention may further comprise other surfactants which should however not significantly alter the weighted average HLB value of the overall composition. Depending on their HLB value said surfactants would be add either in the hydrophilic mixture or in the hydrophobic mixture of the process of the present invention.

The compositions obtained according to the process of the present invention are aqueous. Accordingly, these compositions comprise from 10% to 95% by weight of the total composition of water, preferably from 30% to 90%, most preferably from 50% to 80%. Deionized water is preferably used.

It has been found that the pH of a composition obtained according to the process of the present invention influences its stability. Bleaching ingredients being present in the compositions obtained according to the process of the present invention, it is of course necessary, for chemical stability purpose to formulate said compositions at a pH as is of from 0 to 4. The pH of the compositions can be trimmed by all means available to the man skilled in the art such as inorganic acid (e.g. sulphuric acid) or organic acid or mixtures thereof. The pH may be adjusted at different stages of the process of the present invention. Highly preferred in the process of the present invention is to adjust the pH of the hydrophilic mixture to the desired value before mixing said hydrophilic mixture with the hydrophobic mixture.

The preferred compositions obtained according to the process of the present invention may further comprise a bleach activator. By bleach activator, it is meant herein any compound which reacts with hydrogen peroxide to form a peracid. In the case of bleach activators, such hydrophobic bleach activators typically belong to the class of esters, amides, imides, or anhydrides. A particular family of bleach activators of interest in the present invention were disclosed in applicant's co-pending European patent application No 91870207.7. Particularly preferred in that family is acetyl triethyl citrate which was also disclosed in the context of bar soaps in FR 2 362 210. Acetyl triethyl citrate has the advantages that it is environmentally friendly as it eventually degrades into citric acid and alcohol. Furthermore, acetyl triethyl citrate has a good hydrolytical stability in the product upon storage and it is an efficient bleach activator. As used herein and unless otherwise specified, the term bleach activator includes mixtures of bleach activators.

In the preferred embodiment of the present invention, wherein the compositions obtained according to the process of the present invention comprise among other hydrophobic ingredients a bleach activator which is a hydrophobic liquid ingredient, the surfactant system to be chosen to emulsify said hydrophobic ingredients depends on the HLB value of said ingredients. Accordingly, a suitable way to proceed is to determine the HLB value of the ingredients, then select both the hydrophobic surfactants which have HLB values below said HLB value of said hydrophobic ingredients and the hydrophilic surfactants which have HLB values above said HLB value of said hydrophobic ingredients, wherein the difference in the HLB values of said hydrophobic and hydrophilic nonionic surfactants is at least 1, preferably at least 3.

In a preferred embodiment comprising hydrophobic ingredients among which a hydrophobic bleach activator, the emulsifying system meets the equation:

$$HLB(X) = \frac{\%A}{100} \times HLB(A) + \frac{\%B}{100} \times HLB(B) \text{ and } \%A + \%B = 100\%;$$

where X refers to the hydrophobic ingredients to emulsify, A refers to one of said nonionic surfactants (hydrophilic or hydrophobic), and B refers to the other said nonionic surfactant (hydrophilic or hydrophobic).

In a particularly preferred embodiment of the present invention, wherein the compositions comprise acetyl triethyl citrate as the bleach activator and the hydrophobic peracid, an adequate nonionic surfactant system would comprise a hydrophobic nonionic surfactant with for instance an HLB of 6, such as a Dobanol® 23-2 and a hydrophilic nonionic surfactant with for instance an HLB of 15, such as a Dobanol® 91-10. Another suitable nonionic surfactant system comprises a Dobanol® 236.5 (HLB about 12) and a Dobanol® 23 (HLB below 6).

The compositions obtained according to the process of the present invention are particularly useful as laundry detergent, as laundry pretreaters, i.e. compositions which are dispensed and left to act onto fabrics before they are washed, or as laundry additives to be used together with detergents to boost their performance. These compositions may also be particularly suitable as dishwashing compositions to be used either in the dishwashing machines or by hand, or as carpet cleaners to be used either by direct application onto the carpets or in carpet cleaning machines, or as toilet bowl cleaners or as hard surface cleaners or as denture cleaners.

The present invention will be further illustrated by the following examples.

1) Experimental data demonstrating faster preparation with higher yields of peracids obtained according to the process of the present invention By carrying out processes wherein different peracid precursors, (i.e. processes where the precursors used were in an acid form and processes where the precursors used were in an anhydride form), were mixed with a concentrated hydrogen peroxide solution to form peracid-comprising compositions, the results listed in the following table were obtained.

The concentrated hydrogen peroxide solution used was a solution containing 36% by weight of hydrogen peroxide. These reactions were done at a temperature of 30° C. and at a pH of 1.1. Also, these reactions were done, unless otherwise specified, in presence of 0.036M of sulfuric acid which has the ability to catalyze (i.e. make faster) the peracid formation.

The following equation is applied to calculate the peracid yield:

(peracid concentration/corresponding precursor peracid concentration)*100=% yield In said equation the concentration are expressed in mole/liter.

To determine the peracid concentration the test method described in the article by prof. Di Furia et alt., mentioned herein before, was used. Indeed, 10 ml of composition to be analyzed were added to 10 ml. of an ethanolic standard solution of p-tolyl-methyl-sulfide equimolar with the peracid precursor in the composition to be analyzed (e.g. anhydride or acid) and chromatographic standard (n-eicosane). After 5–10 minutes, 10 gr. of ice, 10 ml of saturated bisulfite solution, 10 ml of saturated bicarbonate solution and finally 10 gr. of sodium chloride were added in the order. The p-tolyl-methyl-sulfoxide formed, the residual p-tolyl-methyl-sulfide and the chromatographic standard were extracted with chloroform (3×20 ml) and the organic layer was concentrated by vacuum evaporation to 5 ml. The amount of sulfoxide produced, corresponding to the percarboxylic acid formed in the reaction was determined by GLC analysis on FFAP 3% on chromosorb W AW DMCS column (30 cm). The response factor of each compound versus the chromatographic standard was separately calculated.

To determine the precursor peracid concentration the amount of anhydride used (or the amount of acid used) in the process mentioned herein before was weighted and expressed in concentration mole liter considering the concentrated hydrogen peroxide solution used.

The table below lists the results obtained:

| Peracid precursors | Time to reach maximum peracid concentration (hours) | Peracid yield (%) |
|---|---|---|
| Citric acid | 50 | 3.5 |
| Tartaric acid | 8 | 2.2 |
| Lactic acid | 12 | 1.5 |
| Glutaric acid | 20 | 14 |
| Glutaric anhydride (without catalyst) | 5 minutes | 60 |
| Acetic acid* | 18 | 17 |
| Acetic anhydride* | 4 | 53 |
| Acetic acid* (without catalyst) | 150 | 9.3 |
| Acetic anhydride* (without catalyst) | 5 | 57 |

* the pH was 0.96

Comments

These data clearly show the advantages of a process according to the present invention, i.e. a faster preparation of peracids as well as higher yields of said peracids.

Indeed, the time needed to reach the maximum peracid concentration (time needed to obtain entirely peroxidation of the anhydride group or groups) in the obtained peracid-comprising compositions, starting from a given amount of peracid precursor is shorter when reacting an anhydride, as said precursor, with a concentrated hydrogen peroxide solution as compared to reacting the corresponding acid with said concentrated hydrogen peroxide solution, this even without the presence of a catalyst, (see in particular data with glutaric anhydride as compared to the data with glutaric acid, i.e. 5 minutes versus 20 hours, as well as data with acetic anhydride as compared to the data with acetic acid, i.e. 5 hours versus 18 hours).

Also higher yields of peracids are obtained with a process of the present invention, i.e. by reacting a given amount of an anhydride, as said precursor, with a concentrated hydrogen peroxide solution, as compared to reacting in presence of a catalyst, the corresponding acid with said concentrated hydrogen peroxide solution (see data with glutaric anhydride as compared to the data with glutaric acid, i.e. 60% yield versus 14% yield, as well as data with acetic anhydride as compared with acetic acid, i.e. 57% yield versus 17% yield).

Indeed, these data clearly show that faster preparation of peracids as well as higher yields of said peracids are obtained according to a process of the present invention, this surprisingly without the need of a catalyst. Also the data show that the reactions done with anhydrides as peracid precursors are much less dependent from the acid catalyst.

2) Experimental data demonstrating higher yields of peracids in emulsions obtained according to the process of the present invention Another experiment was carried out wherein the process of the present invention for manufacturing an emulsion comprising the step of mixing the corresponding anhydride with a concentrated hydrogen peroxide solution to obtain a peroxide-comprising composition, followed by dilution and emulsification, was compared to a conventional process. By said conventional process the same emulsion was prepared but the corresponding anhydride was put into said emulsion without a preliminary reaction with a concentrated hydrogen peroxide solution.

The concentrated hydrogen peroxide solution used in the process according to the present invention for manufacturing said emulsion was a solution comprising 70% by weight of said hydrogen peroxide. Both processes, i.e. the one according to the present invention and the conventional one, were carried out at room temperature.

The following yields of peracid (%) were obtained in both final emulsions:

| Peracid precursors | Process according to the present invention | Conventional process |
|---|---|---|
| Glutaric anhydride (0.175M) | 68 | 21 |

Accordingly the emulsion obtained according to the process of the present invention contained the following ingredients in the following proportions (% by weight):

| | | |
|---|---|---|
| Dobanol 91-10 | 1.2% | |
| Dobanol 91-2.5 | 4.8% | |
| Hydrogen peroxide | 7% | |
| Perglutaric acid | 1.76% | |
| Citric acid | 6% | |
| Sulfuric acid | 1.9% | |
| Perfume | 0.5% | |

Comments

These data clearly show that the process according to the present invention allows to obtain 68% yield of peracid in a given emulsion while for the conventional process only 21% of yield of peracid is obtained in said emulsion, starting from a same amount of corresponding anhydride. Indeed, the process according to the present invention provide emulsions where the peracid concentration is higher than what can be achieved by simply mixing the anhydride directly in the final emulsion.

3) Stability data

Stability data has been provided for the above mentioned emulsion containing glutaric peracid generated from glutaric anhydride according to the process of the present invention as compared to a similar composition also prepared according to the process of the present invention but being not in the form of an emulsion.

In said emulsion the time required to have half of its initial peracid concentration (T1/2) was 21 hours while in the corresponding composition the time required to have half of its initial peracid concentration (T1/2) was 11 hours.

The calculation of T1/2 has been done by plotting data on peracid decomposition as a function of time. On the decomposition curve obtained the peracid concentration at T1/2 has been extrapolated. The glutaric peracid concentration can be measured as per the article mentioned herein above.

We claim:

1. A process for manufacturing an aqueous composition comprising a peracid, or mixture thereof, wherein said peracid is emulsified in a surfactant system comprising at least a hydrophilic surfactant having an HLB above 11, and a hydrophobic surfactant having an HLB below 11, said process comprising the steps of:

1—preparing an aqueous peracid-comprising composition by a process which comprises the step of forming said peracid by reacting the corresponding anhydride with a solution of hydrogen peroxide comprising at least about 3 moles of said hydrogen peroxide per molar equivalent of said corresponding anhydride, wherein said corresponding anhydride is selected from anhydrides having the following formula:

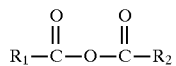

wherein $R_1$ and $R_2$ are linear or branched alkyl groups having of from 1 to about 20 carbon atoms, said anhydrides being symmetric anhydrides or asymmetric anhydrides;

2—preparing a hydrophobic mixture which comprises at least said hydrophobic surfactant;

3—preparing a hydrophilic mixture which comprises at least water and said hydrophilic surfactant;

4—mixing the composition obtained in step 1 in said hydrophilic mixture if said corresponding anhydride used in step 1 is an anhydride having the following formula:

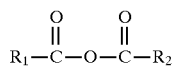

wherein $R_1$ and $R_2$ are linear or branched alkyl groups having of from 1 to 4 carbon atoms, said anhydrides being symmetric anhydrides or asymmetric anhydrides or in said hydrophobic mixture if said corresponding anhydride used in step 1 is an anhydride having the following formula:

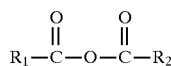

wherein $R_1$ and $R_2$ are linear or branched alkyl groups having of from 5 to about 20 carbon atoms, said anhydrides being symmetric anhydrides or asymmetric anhydrides 5—then mixing together said hydrophobic mixture and said hydrophilic mixture, and wherein steps 2 and 3 may be performed in any order.

2. A process according to claim 1 for manufacturing an aqueous composition wherein said composition comprises from, about 0.01% to about 30% by weight of said peracid and from 0.5% to 20% by weight of said hydrogen peroxide.

3. A process according to claim 1 for manufacturing an aqueous composition wherein said composition comprises from about 0.1% to about 20% by weight of said peracid, and from 2% to 15% by weight of said hydrogen peroxide.

4. A process according to claim 1 for manufacturing an aqueous composition comprising a peracid, or mixtures thereof, wherein said peracid is emulsified in a surfactant system comprising at least a hydrophilic surfactant having an HLB above 12 and a nonionic surfactant having an HLB below 10.

* * * * *